US00PP19828P2

(12) United States Plant Patent
Austin

(10) Patent No.: US PP19,828 P2
(45) Date of Patent: Mar. 17, 2009

(54) ***ROSA HYBRIDA* SHRUB NAMED 'AUSMERCHANT'**

(50) Latin Name: *Rosa hybrida*
Varietal Denomination: AUSmerchant

(75) Inventor: David C. H. Austin, Wolverhampton (GB)

(73) Assignee: David Austin Roses Ltd., Wolverhampton (GB)

( * ) Notice: Subject to any disclaimer, the term of this patent is extended or adjusted under 35 U.S.C. 154(b) by 0 days.

(21) Appl. No.: 12/001,100

(22) Filed: Dec. 10, 2007

(51) Int. Cl.
*A01H 5/00* (2006.01)

(52) U.S. Cl. ..... Plt./107
(58) Field of Classification Search ..... Plt./107
See application file for complete search history.

(56) References Cited

FOREIGN PATENT DOCUMENTS

GB AFP 5/2101 * 10/2007

* cited by examiner

*Primary Examiner*—Kent L Bell
(74) *Attorney, Agent, or Firm*—Kauth, Pomeroy, Peck & Bailey LLP

(57) ABSTRACT

A variety of rose plant of the shrub class, named 'AUSmerchant' is disclosed. The 'AUSmerchant' rose is a plant suitable for repeat flowering production having large pink blooms and a strong tea fragrance.

1 Drawing Sheet

Classification: The present invention relates to a new *Rosa hybrida* shrub.

Variety denomination: The new plant has the varietal denomination 'AUSmerchant'.

ORIGIN OF INVENTION

This invention relates to a new and distinct variety of shrub rose plant named 'AUSmerchant', which was originated by crossing two unnamed, unpatented varieties of *Rosa hybrida.*

BACKGROUND OF THE INVENTION

The primary objective of this breeding was to produce a very healthy repeat flowering variety having large, pink blooms with a strong fragrance and strong rounded growth.

SUMMARY OF THE INVENTION

Among the features which distinguish the new variety from other presently available and commercial rose cultivars known to the inventor is the following combination of characteristics: large, pink blooms with a strong fragrance and strong rounded growth.

Asexual reproduction of the new variety by budding as performed in greenhouses at Bowling Green Lane in Albrighton, Britain shows that the foregoing and other distinguishing characteristics come true to form and are established and transmitted through succeeding asexual propagations. 'AUSmerchant' may be asexually propagated by budding and grafting. The budding and grafting successfully occurred on the plant/rootstock *Rosa* cv. 'Dr. Huey' in the United States and on the plant/rootstock *Rosa dumetorum* cv. 'Laxa' in the United Kingdom.

COMPARISON WITH PARENTS

The new rose may be distinguished from its seed parent, by the following combination of characteristics: whereas the parent has bright crimson blooms and very little fragrance, 'AUSmerchant' bears flowers of pink and a strong fragrance. The new variety is classified as a *hybrida* rose with a strong rounded growing habit.

The new variety may be distinguished from its pollen parent, by the following combination of characteristics: whereas the pollen parent bears rich crimson blooms, 'AUSmerchant' bears flowers of a warm pink.

COMPARISON WITH THE CLOSEST COMMERCIALLY AVAILABLE CULTIVAR

The closest commercially available cultivar to the new variety is the 'AUShunter', which is unpatented. The new rose may be distinguished from the 'AUShunter' variety by the following combination of characteristics: the 'AUShunter' has fewer petals, smaller blooms with a salmon color and darker leaves compared to 'AUSmerchant', which has a greater number of petals, warm pink blooms and lighter green leaves.

BRIEF DESCRIPTION OF ILLUSTRATION

The accompanying photograph illustrates the new variety and shows the flowering thereof from bud to full bloom depicted in color as nearly correct as it is possible to make in a color illustration of the character. Throughout this specification, color references and/or values are based upon the Colour Chart of The Royal Horticultural Society (2001) except where common terms of color definition are employed.

DESCRIPTION OF THE NEW VARIETY

The following description is of 2 year-old rose plants of the new variety grown outdoors in Albrighton, Britain in the month of August. Phenotypic expression may vary with environmental, cultural and climatic conditions, as well as differences in conditions of light and soil.

Flower characteristics:

*Blooming habit.*—Recurrent. The number of blooms per plant during the growing season is profuse, but there are too many to count.

*Bud.*—Size: About 2.5 cm long and 2.5 cm in diameter when the petals start to unfurl. Form: The bud form is globular. Color: When sepals first divide, the bud color is Red Group 46A. When half blown, the upper sides of the petals are Orange-Red Group 31B, and the lower sides of the petals are Red Group 42C. Calyx: Shape: (from above) irregularly rounded. Length: 1.8 cm. Diameter: 2 cm. Sepals: Arrangement: Regular. Color: Upper Surface: Green Group 138C. Lower Surface: Green Group 138B. Length: 2.2 cm. Width: 1.3 cm. Shape: Subulate. Surface texture: Upper Surface: Pubescent. Lower Surface: Smooth, glossy. Number: There are three lightly appendaged sepals. There are 2 unappendaged. Apex: Sepal apex has weak extensions. Margin: The typical and observed unappended sepals have smooth edges. Receptacles: Color: Green Group 138A with irregular patches of Greyed-Purple Group 183A. Shape: Funnel. Size: small, about 1 cm×1.4 cm. Surface: Smooth. Peduncle: Length: long, averaging about 15 cm. Diameter: about 3 mm. Surface: Smooth. Color: Yellow-Green Group 144A overlaid with patches of Greyed-Red Group 178A. Strength: Strong.

*Blooms.*—Size: Very large, average open diameter is about 11 cm. Depth: Typical and observed bloom depth is about 5 cm. Borne: In clusters of 1–4 blooms having corymb shaped inflorescence. Stems: Strength: Normal, average length is about 40–50 cm. Diameter: 3 mm. Form: When first open, bloom is cupped. Permanence of bloom: Retains its form to the end.

*Petalage.*—Number of petals under normal conditions: 130. Color: The upper sides of the petals are Red Group 54A. The reverse sides of the petals are Red Group 54A. The base of the petals is Orange-Red Group 35B. Discoloration: The general tonality at the end of the first day is: Red Group 54A. At the end of the third day is: Red-Purple Group 68B. Fragrance: Strong. Character of fragrance: Tea becoming lemon. Lastingness: The cut flower has an average lastingness of about 3 to 4 days.

*Petals.*—Texture: Smooth, satiny. Size: Width: 2.9 cm. Length: 4 cm. Surface: Smooth. Shape: Obovate. Margin: Notched. Apex Shape: Emarginate. Base Shape: Pointed. Form: Incurved, some tips slightly recurved. Arrangement: Informal. Petaloids: Number: 7–10. Color: Petal: Purple Group 75A; Anther: Yellow-Orange Group 20A; Filament: Yellow-Orange Group 15A. Length: Petal: 18 mm. Anther: 2 mm. Filament: 5 mm. Width: Petal only: 15 mm. Shape: Irregular. Margin: Irregular. Persistence: Petals hang on and dry. Lastingness: On the plant: fair, about 5 days. As a cut flower: not tested.

*Reproductive Parts.*—Stamens: Number: 75. Length: 7 mm. Anthers: Length: 2 mm. Color: Yellow-Orange Group 20A. Arrangement: Mixed with petaloids. Filaments: Color: Yellow-Orange Group 15A. Length: 5 mm. Pollen: Color: Yellow-Orange Group 21A. Pistils: Number: 90. Length: 10 mm. Styles: Color: Yellow-Green Group 154D. Length: 10 mm. Stigmas: Color: Yellow-Orange Group 15A. Length: 1 mm. Hips: None Observed.

Plant characteristics:

*Plant form.*—Shrub.

*Plant growth.*—Medium vigor and bushy.

*Age to maturity.*—Two years.

*Mature plant.*—Height: 1 m. Width: 0.75 m.

*Rootstock.*—*Rosa* 'Dr. Huey' for U.S. and *Rosa dumetorum* cv. 'Laxa' for observed plants in the U.K.

*Foliage.*—Number: Leaflets on normal mid-stem leaves is: 5–7 (including terminal leaflet). Size: Medium, about 14 cm long×8.75 cm wide. Quantity: Normal. Number of leaves per flowering stem is: 8–10. Color: New foliage: Upper side: Greyed-Purple Group 183B. Lower side: Greyed-Purple Group 183B. Old foliage: Upper side: Green Group 137A. Lower side: Green Group 137B.

*Leaflets.*—Size: About 4.6 cm long×4 cm wide. Shape: Broadly oval. Base Shape: Rounded. Apex Shape: Cuspidate. Texture: Smooth. Edge: Serrated. Serrations: Double. Petiole: Color: Green Group 137B. Length: 4 cm. Width: 2 mm. Surface Texture: Prickly. Petiole Rachis: Color: Green Group 137B. Underside: with prickles. Stipules: Length: 9.5 cm, serrated/glandular. Color: Green Group 137B. Auricle: Shape: Awl-shaped. Length: 10–15 mm. Width: 2 mm at base tapering to point. Color: Green Group 137B. Vein Color: Yellow-Green Group 145C. Venation Pattern: Reticulate.

*Wood.*—New Wood: Color: Greyed-Purple Group 185A. Bark: Smooth. Old Wood: Color: Green Group 143A. Bark: Smooth.

*Branching habit.*—Number: 2 per main stem. Lateral Branch Dimensions: Length: 24 cm. Diameter: 5 mm.

*Stems.*—Mature Stem: Length: 90 cm. Diameter: 4 mm. Color: Green group 143A. Internode Distance: 12 cm. The above measurements are all variable, depending on growing conditions in a season. Stem Pubescence Present: No.

*Prickles.*—Quantity: On main canes from base: ordinary. Number per stem length: 7 per 5 cm. On laterals from main canes: few. Number per stem length: 5 per 5 cm. Form: Hooked downward. length: 10 mm. Color when young: Greyed-Purple Group 183C. Color when mature: Greyed-Brown Group 199B.

*Small prickles.*—Quantity: Main stalk: Few. Number per stem length: 3 per 10 cm. Laterals: Few. Number per stem length: 3 per 10 cm (bottom third of stem only). Color: When young: Greyed Purple Group 183C. When mature: Greyed-Brown Group 199B.

*Disease resistance.*—Mildew: Resistant to both Powdery Mildew and Downy Mildew. Blackspot: Resistant. Rust: Resistant.

*Pest resistance.*—Not tested.

*Winter hardiness.*—Not tested.

*Growing conditions.*—Normal conditions for a garden rose, namely, outdoors in soil.

What is claimed is:

1. A new and distinct variety of rose plant of the shrub class suitable for repeat flower production, substantially as herein shown and described.

* * * * *

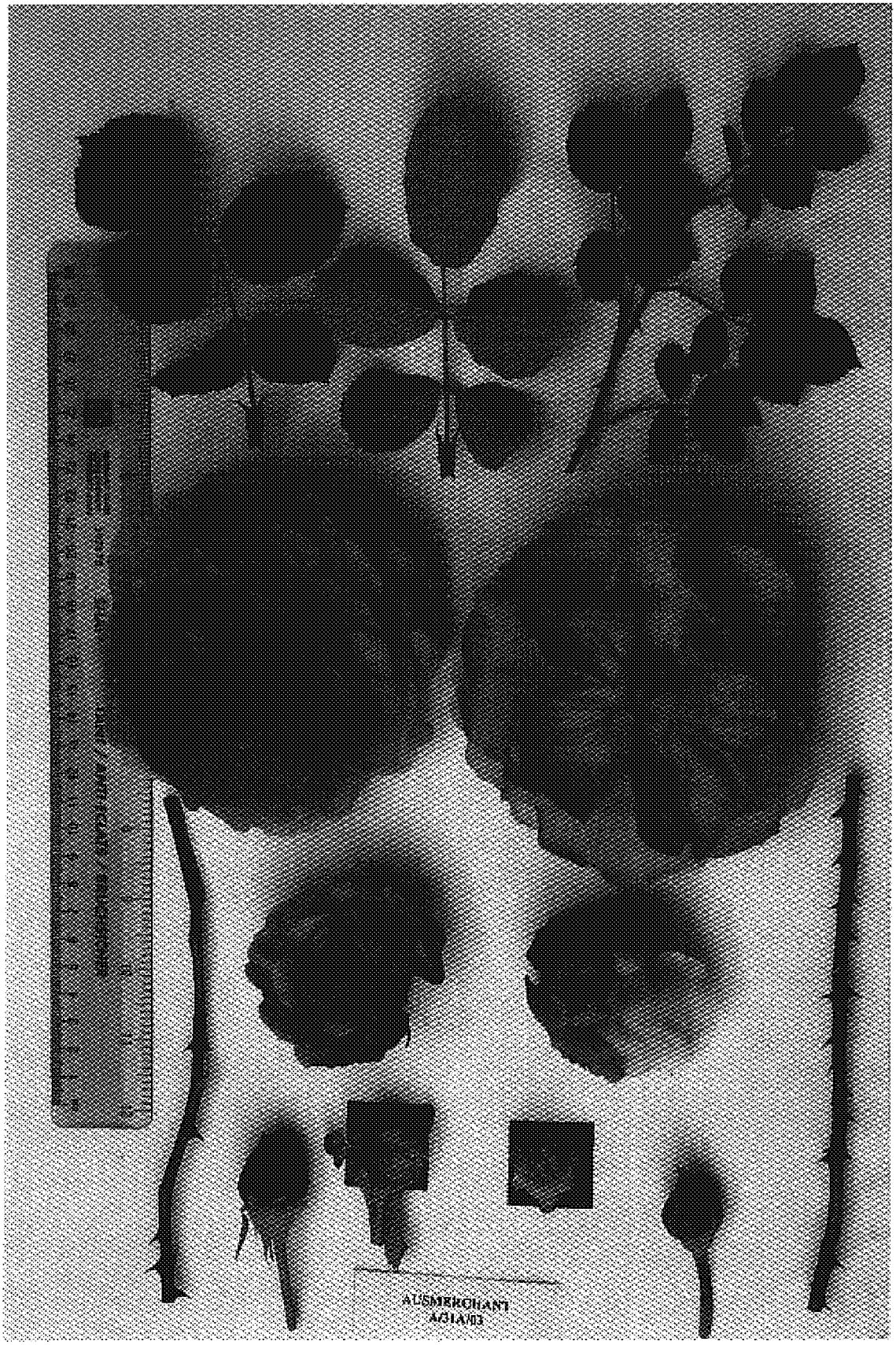
AUSMERCHANT
A/31A/03